United States Patent [19]

Abercrombie

[11] Patent Number: 4,605,065
[45] Date of Patent: Aug. 12, 1986

[54] METHOD AND APPARATUS FOR MONITORING WELL TUBING FLUID

[75] Inventor: Bolling A. Abercrombie, Montgomery County, Tex.

[73] Assignee: Hughes Tool Company, Houston, Tex.

[21] Appl. No.: 748,785

[22] Filed: Jun. 26, 1985

[51] Int. Cl.⁴ .................. E21B 41/02; E21B 47/00
[52] U.S. Cl. ........................ 166/250; 73/86; 166/117.5; 166/902; 166/381
[58] Field of Search .............. 166/117.5, 250, 902, 166/381, 382, 113; 73/86, 151, 432 R

[56] References Cited

U.S. PATENT DOCUMENTS

| | | | |
|---|---|---|---|
| 3,996,124 | 12/1976 | Eaton et al. ................. | 73/86 X |
| 4,105,279 | 8/1978 | Glotin et al. ................ | 166/117.5 X |
| 4,120,313 | 10/1978 | Lewis ......................... | 73/86 |
| 4,483,397 | 11/1984 | Gray .......................... | 166/250 |
| 4,501,323 | 2/1985 | Lively et al. ................. | 166/250 |

Primary Examiner—Stephen J. Novosad
Attorney, Agent, or Firm—H. Dennis Kelly

[57] ABSTRACT

A method and apparatus for monitoring corrosive effects of fluid in a well, for use with a well tubing mandrel having a main bore and a side pocket offset from the main bore. The mandrel also has a slot along the length of the side pocket adjacent the main bore, and the exterior surface of the mandrel is free of apertures. A corrosion coupon is mounted within a notch on the side of a carrier, and the carrier is placed into the side pocket for a specified time period. The carrier is oriented to position the coupon within the slot. The carrier is then removed from the well and the coupon is inspected.

10 Claims, 5 Drawing Figures

METHOD AND APPARATUS FOR MONITORING WELL TUBING FLUID

BACKGROUND OF THE INVENTION

1. Field of the Invention

This invention relates in general to methods and devices for monitoring the corrosion characteristics of tubing fluid in a producing well, and in particular to an improved method and device for monitoring the corrosion characteristics of well tubing fluids by installing a monitoring device downhole in a side pocket mandrel.

2. Description of the Prior Art

Oil and gas wells normally contain several concentric metal conduits extending from the bottom of the well to the surface. The inner conduits are known as well tubing, and the outermost conduit is known as the well casing. Various fluids flow, or are pumped, upwardly or downwardly within the innermost tubing or within the annular spaces between conduits.

Fluid within the tubing, i.e., tubing fluid, may be highly corrosive to the steel tubing. For example, carbon dioxide and hydrogen sulfide are common corrosives in many oil and gas wells. Tubing failure because of corrosion may necessitate an extensive workover. In order to combat corrosion, various chemicals may be injected into the well or into the producing formation to inhibit the corrosive action of the well fluids on the steel tubing.

The injection of corrosion inhibitors into a well has at times been unsuccessful because of the failure of the solution to completely coat the metal to be protected. U.S. Pat. No. 3,385,358 (Shell) shows a monitoring device used to inspect for total coverage. A tracer material is included in the inhibitor solution prior to injection. Then, after injection, a radioactivity detector is lowered into the well on a wireline to monitor the coverage of the inhibitor solution.

Another method of monitoring the effectiveness of corrosion inhibitors is to insert metal coupons into the fluid for a specified time and then inspect the coupons. A method and apparatus for inserting coupons into a surface pipeline is described in U.S. Pat. No. 4,275,592 (Atwood). That method is excellent for monitoring fluid in a surface pipeline, but the corrosive effects of the fluid in the surface pipeline may be much different from the corrosive effects of the fluid downhole.

Corrosion monitoring coupons can be placed downhole by lowering a coupon carrier down the tubing string on a wire line. However, the device partially blocks the flow of fluid through the tubing, and the device must be removed before other tools can be run down the tubing.

U.S. Pat. No. 4,501,323 (Lively et al.) shows a method for monitoring fluids downhole by installing corrosion coupons within a carrier, which is then placed within a side pocket mandrel. Ports and passages allow casing fluid or tubing fluid to communicate with various coupons. The carrier is left within the side pocket mandrel for a specified time period. The carrier is then removed from the well, and the coupons are inspected.

U.S. Pat. No. 4,483,397 (Gray) shows a similar method and apparatus for monitoring tubing fluid downhole in an oil or gas well. Corrosion coupons are installed in a carrier which is placed in a side pocket mandrel. The outer surface of the mandrel is free of apertures, so only tubing fluid can be monitored. Ports and passages in the side pocket and in the carrier allow tubing fluid to communicate with the coupon. After the carrier has been in the side pocket for a specified time period, the carrier is removed from the well, and the coupons are inspected.

SUMMARY OF THE INVENTION

The invention is an improved method and apparatus for monitoring tubing fluid in a well at points downhole, such as near the point at which a corrosion inhibiting solution has been injected into the producing formation or into the well tubing or casing.

A well tubing mandrel is installed in the well tubing at the point downhole at which monitoring is desired. The mandrel has a main bore and a side pocket offset from the main bore. This type of mandrel is thus known as a side pocket mandrel. The mandrel has an open slot between the main bore and the side pocket, but the exterior surface of the mandrel is free of apertures.

A corrosion monitoring coupon is then mounted onto a cylindrical coupon carrier. The coupon is a rectangular, flat strip of a selected material, usually the same type steel as the tubing. The coupon carrier is cylindrical and has a rectangular notch on one side, to which the coupon is attached. The coupon carrier is then run down the tubing and inserted into the side pocket of the mandrel using a conventional kickover tool and other related tools. The carrier is detached from the kickover tool and the tool is removed from the well. For a specified time the carrier is left in the side pocket with the coupon in communication with the tubing fluid. The coupon carrier is oriented within the side pocket so that the coupon is positioned within the slot between the main bore and the side pocket. The coupon thus simulates a portion of the tubing wall. At the end of the test period, the kickover tool is used to retrieve the carrier and remove it from the well. The coupon can then be inspected to determine the effectiveness of the corrosion inhibitor.

The above as well as additional objects, features, and advantages of the invention will become apparent in the following detailed description.

DESCRIPTION OF THE PREFERRED EMBODIMENT

Figure 1:
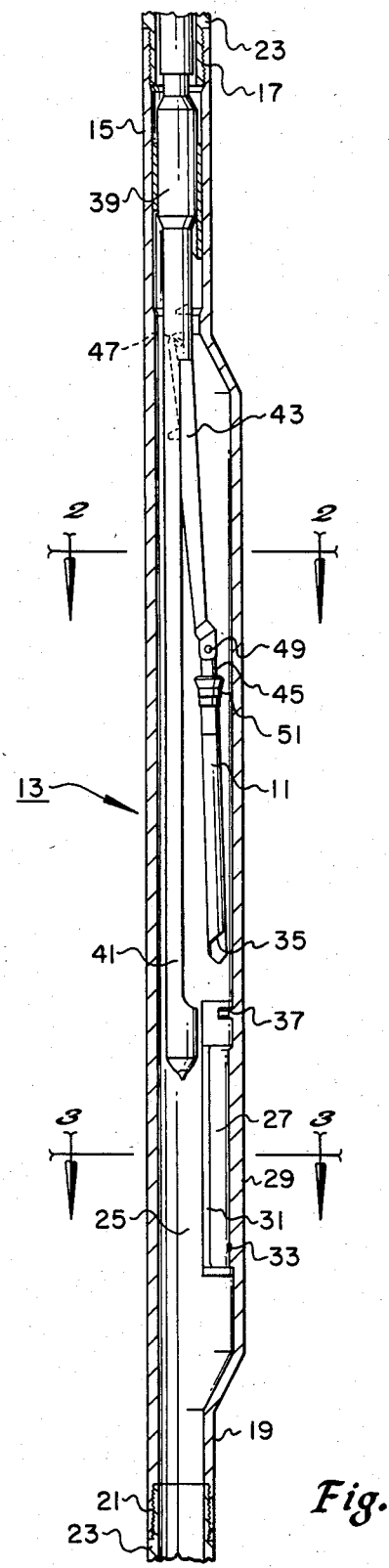
FIG. 1 is a sectional view of a side pocket mandrel and a kickover tool installing or removing a coupon carrier.

FIG. 1 of the drawings illustrates a coupon carrier 11 being inserted into or being removed from a well tubing mandrel 13. At the upper end, the mandrel 13 has a cylindrical portion 15 with threads 17, and at the lower end, the mandrel 13 has another cylindrical section 19 with threads 21. The threads 17, 21 are a connection means for connecting the mandrel within well tubing 23 downhole.

Between the two cylindrical portions 15, 19, the mandrel 13 has a main throughbore 25 which is aligned with the cylindrical portions 15, 19 and the well tubing 23, and is approximately the same size. The mandrel 13 also has a side pocket 27 which is offset from the main bore 25, and housed within a side pocket housing 29.

A milled slot 31 is located between the main bore 25 and the side pocket 27. A guide pin 33 is located near the bottom of the side pocket housing 29 opposite the milled slot 31. The guide pin 33 acts against a helical sloping surface 35 which ends in a slot on the coupon carrier 11 to orient the coupon carrier 11 in the side pocket housing 29.

Near the upper end of the side pocket housing, a latch retainer 37 is formed by a reduction in the internal diameter of the side pocket 27. The latch retainer 37 is a latch means for releasably retaining the carrier 11 in the side pocket 27. The coupon carrier 11 is inserted and removed by a kickover tool 39 of a type well known in the art. The kickover tool 39 includes a guide case 41, a shifting tool 43, and a carrier handling support 45. The shifting tool 43 is pivotally attached to the guide case 41 at the pin 47, and the carrier handling support 45 is pivotally attached to the shifting tool 43 at pin 49. The carrier handling support 45 is detachably connected to a latch assembly 51, which is in turn secured to the carrier 11.

Figure 2:
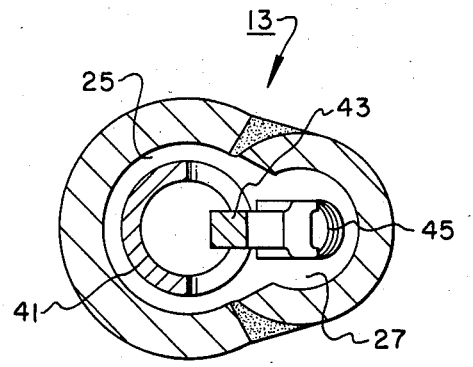
FIG. 2 is a sectional view of a side pocket mandrel as seen along lines II—II of FIG. 1.

FIG. 2 of the drawings is a sectional view as seen along lines II—II of FIG. 1. The guide case 41 is located in the main bore 25 of the mandrel 13, while the shifting tool 43 has moved the carrier handling support 45 over into alignment with the side pocket 27.

Figure 3:
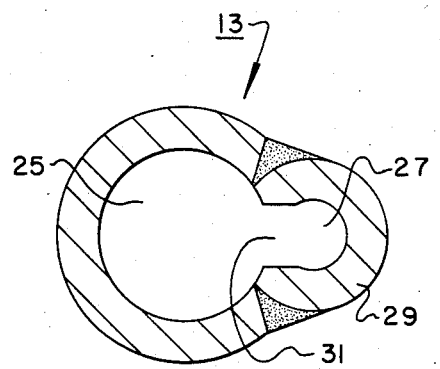
FIG. 3 is a sectional view of a side pocket mandrel as seen along lines III—III of FIG. 1.

FIG. 3 is a sectional view as seen along lines III—III of FIG. 1. The side pocket 27 is offset from the main bore 25 and a milled slot 31 is located between the main bore 25 and the side pocket 27.

Figure 4:
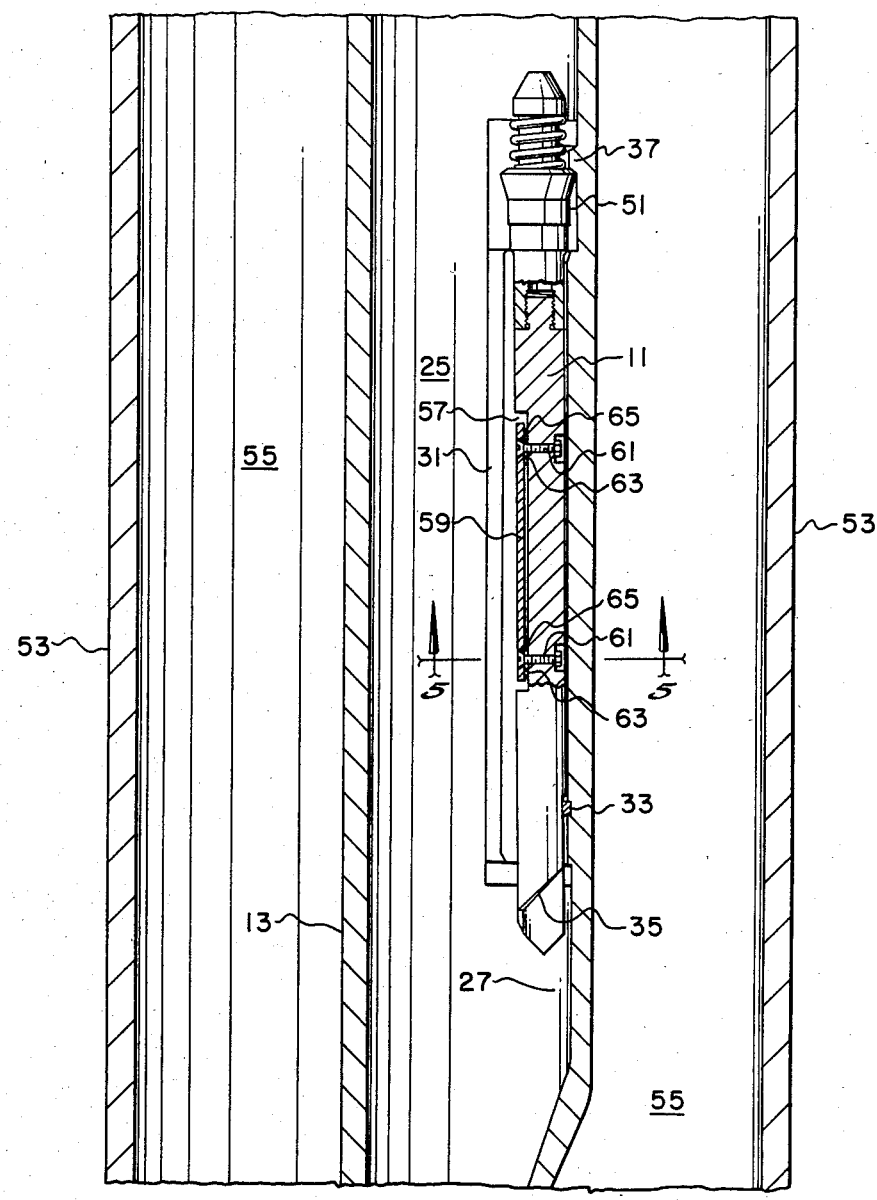
FIG. 4 is a sectional view of a side pocket mandrel with a coupon carrier in place in the side pocket.
Figure 5:
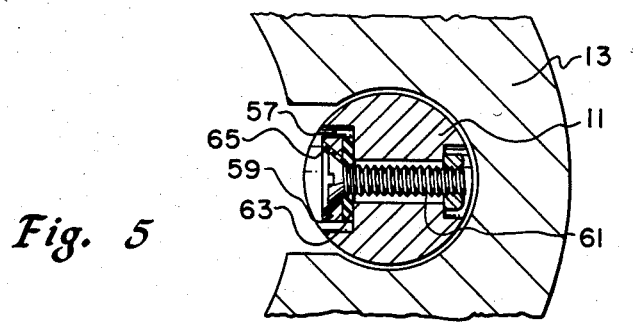
FIG. 5 is a sectional view of a coupon holder as seen along lines V—V of FIG. 4.

FIGS. 4 and 5 illustrate a coupon carrier 11 placed in the side pocket 27. The well tubing mandrel 13 is surrounded by well casing 53, defining an annulus 55 between the mandrel 13 and the casing 53. The side pocket 27 is offset from the main bore 25, which is aligned with the cylindrical portions 15, 19 and the well tubing 23 (shown in FIG. 1).

The coupon carrier 11 is generally cylindrical, but has a rectangular notch 57 on one side. A corrosion monitoring coupon 59 is mounted in the notch 57 by a pair of coupon holders 61. Insulators 63 insulate the coupon 59 from the coupon carrier 11, and head insulators 65 insulate the coupon 59 from the coupon holders 61. The coupon 59 is rectangular strip coupon, and when the coupon carrier 11 is properly oriented in the side pocket 27, the coupon 59 is positioned in the slot 31 between the main bore 25 and the side pocket 27. The coupon 59 thus simulates a wall of the main bore 25.

In operation, the well tubing mandrel 13 is installed in a string of well tubing 23, so that when the well tubing 23 is in place downhole, the mandrel 13 will be at the depth at which it is desired to monitor the tubing fluid. A coupon 59 is then attached to a coupon carrier 11 by coupon holders 61.

The coupon carrier 11 is connected to a latch assembly 51, which is then attached to the carrier handling support 45 of a standard kickover tool 39. The kickover tool 39 is then maneuvered so that the shifting tool 43 moves the carrier 11 over into alignment with the side pocket 27. The carrier 11 is then lowered into the side pocket 27. As the carrier 11 is lowered into the side pocket 27, the guide pin 33 acts against the sloping surface 35 on the coupon carrier 11 to properly orient the carrier 11 within the side pocket housing. The guide pin 33 and the sloping surface 35 are thus an orienting means for orienting the carrier 11 to position the coupon 59 within the slot 31 between the main bore 25 and the side pocket 27.

The latch assembly 51 latches under the latch retainer 37. The carrier handling support 45 releases the latch assembly 51 and the kickover tool 39 is removed from the well. At this point, the carrier 11 is in the position illustrated in FIG. 4.

The coupon 59 is left in the side pocket 27 for a selected time period. During this period, the coupon 59 simulates a wall of the main bore 25. After the carrier 11 has been in the well a specified time, the carrier 11 is removed. The kickover tool 39 is again run down the tubing 23 until it reaches the side pocket mandrel 13. The kickover tool 39 is then maneuvered so that the shifting tool 43 positions the carrier handling support 45 onto the latch assembly 51. The kickover tool 39 is then raised, releasing the latch assembly 51 from the latch retainer 37 and removing the carrier 11 from the well.

The coupon 59 is then removed from the coupon carrier 11 and inspected for corrosion. The corrosive effect of the tubing fluid on the coupon 59 should be somewhat analogous to the corrosive effects of the tubing fluid on the walls of the tubing 23.

While the invention has been described in only one of its forms, it should be apparent to those skilled in the art that it is not so limited, but is susceptible to various changes and modifications without departing from the spirit thereof.

I claim:

1. An apparatus for monitoring corrosive effects of fluid in a well, for use with a well tubing mandrel having a main bore and a side pocket offset from the main bore, the apparatus comprising:
   a carrier, mounted in the side pocket; and
   a coupon secured to the carrier, and positioned within a slot between the main bore and the side pocket.

2. An apparatus for monitoring corrosive effects of fluid in a well, for use with a well tubing mandrel having a main bore and a side pocket offset from the main bore, the apparatus comprising:
   a carrier, mounted in the side pocket;
   a coupon, secured to one side of the carrier; and
   orienting means for orienting the carrier to position the coupon within a slot between the main bore and the side pocket.

3. An apparatus for monitoring corrosive effects of fluid in a well, for use with a well tubing mandrel having a main bore and a side pocket offset from the main bore, the apparatus comprising:
   a cylindrical carrier, mounted in the side pocket, the carrier having a rectangular notch on one side; and
   a coupon, secured to the carrier, within the notch, and positioned within a slot between the main bore and the side pocket.

4. An apparatus for monitoring corrosive effects of fluid in a well, for use with a well tubing mandrel having a main bore and a side pocket offset from the main bore, the apparatus comprising:
   a cylindrical carrier, mounted in the side pocket, the carrier having a rectangular notch on one side;
   a coupon secured to the carrier, within the notch; and orienting means for orienting the carrier to position the coupon within a slot between the main bore and the side pocket.

5. An apparatus for monitoring fluids in a well, comprising:
a well tubing mandrel having connection means for connecting the mandrel within well tubing downhole, a main bore, a side pocket offset from the main bore, and a slot along substantially the entire length of the side pocket adjacent to the main bore, wherein the exterior surface of the mandrel is free of apertures;
a carrier, mounted in the side pocket; and
a coupon secured to the carrier, and positioned within the slot to simulate a section of the tubing.

6. An apparatus for monitoring fluids in a well, comprising:
a well tubing mandrel having connection means for connecting the mandrel within well tubing downhole, a main bore, a side pocket offset from the main bore, and a slot along substantially the entire length of the side pocket adjacent to the main bore, wherein the exterior surface of the mandrel is free of apertures;
a carrier, mounted in the side pocket;
a coupon secured to the carrier; and
orienting means for orienting the carrier to position the coupon within the slot.

7. An apparatus for monitoring fluids in a well, comprising:
a well tubing mandrel having connection means for connecting the mandrel within well tubing downhole, a main bore, a side pocket offset from the main bore, and a slot along substantially the entire length of the side pocket adjacent to the main bore, wherein the exterior surface of the mandrel is free of apertures;
a cylindrical carrier, mounted in the side pocket, the carrier having a rectangular notch on one side; and
a coupon secured to the carrier, within the notch, and positioned within the slot to simulate a section of the tubing.

8. A method of monitoring fluid within well tubing, comprising the steps of:
installing a well tubing mandrel downhole in well tubing, said mandrel having a main bore, a side pocket offset from the main bore, and a slot along the length of the side pocket adjacent the main bore;
mounting a coupon on a carrier, said coupon being a strip of selected material;
placing the carrier into the side pocket, positioning the coupon within the slot for a specified time period;
removing the carrier from the well tubing; and
inspecting the coupon.

9. A method of monitoring fluid within well tubing, comprising the steps of:
installing a well tubing mandrel downhole in well tubing, said mandrel having a main bore, a side pocket offset from the main bore, and a slot along the length of the side pocket adjacent the main bore, the exterior surface of the mandrel being free of apertures;
mounting a coupon within a notch on the side of a carrier, said coupon being a strip of selected material;
placing the carrier into the side pocket, positioning the coupon within the slot for a specified time period;
removing the carrier from the well tubing; and
inspecting the coupon.

10. A method of monitoring fluid within well tubing, comprising the steps of:
installing a well tubing mandrel downhole in well tubing, said mandrel having a main bore, a side pocket offset from the main bore, and a slot along the length of the side pocket adjacent the main bore, the exterior surface of the mandrel being free of apertures;
mounting a coupon within a notch on the side of a carrier, said coupon being a strip of selected material;
placing the carrier into the side pocket for a specified time period, the carrier being oriented to position the coupon within the slot;
removing the carrier from the well tubing; and
inspecting the coupon.

* * * * *